United States Patent [19]

Cowherd, III et al.

[11] 4,167,635
[45] Sep. 11, 1979

[54] N,N-ACRYLOXY ETHOXY PIPERAZINES

[75] Inventors: Frank G. Cowherd, III; Louis F. Theiling, Jr., both of Charleston, W. Va.

[73] Assignee: Union Carbide Corporation, New York, N.Y.

[21] Appl. No.: 936,726

[22] Filed: Aug. 25, 1978

Related U.S. Application Data

[62] Division of Ser. No. 755,063, Dec. 28, 1976, Pat. No. 4,126,747.

[51] Int. Cl.² ............................................ C07D 295/18
[52] U.S. Cl. .................................... 544/388; 548/341; 260/239 A
[58] Field of Search ............... 544/388; 260/239 AR; 548/341

[56] References Cited

U.S. PATENT DOCUMENTS 3,674,838  7/1972  Nordstrom ........................... 560/166
4,126,747  11/1978  Cowherd et al. ..................... 544/388

*Primary Examiner*—Jose Tovar
*Attorney, Agent, or Firm*—Aldo John Cozzi

[57] ABSTRACT

There are claimed novel carbamoyloxy acrylate compounds of the formula

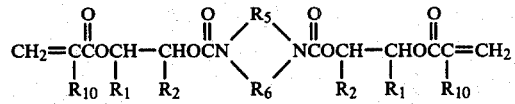

wherein $R_1$ and $R_2$ are each hydrogen or alkyl of up to 10 carbon atoms; $R_5$ and $R_6$ are each methylene, ethylene, or 1,2-propylene; and $R_{10}$ is hydrogen or methyl. The compounds are polymerizable to produce materials useful, for example, in coatings.

2 Claims, No Drawings

N,N-ACRYLOXY ETHOXY PIPERAZINES

This is a divisional application of applicants' copending patent application, Ser. No. 755,063, filed Dec. 28, 1976 now U.S. Pat. No. 4,126,747, issued Nov. 21, 1978.

BACKGROUND OF THE INVENTION

There are known in the prior art, as disclosed in U.S. Pat. No. 3,674,838, unsaturated carbamoyloxy carboxylates having the formula

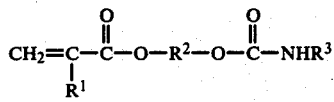

wherein $R^1$ is hydrogen, a monovalent alkyl, aryl or aralkyl hydrocarbon radical free of ethylenic unsaturation of one to eight carbon atoms, or a halogen; $R^2$ is a divalent hydrocarbon radical of one to 12 carbon atoms; and $R^3$ is hydrogen or a lower alkyl radical of one to eight carbon atoms.

These unsaturated compounds are useful as polymerizable monomers, particularly in coating compositions, wherein they serve as viscosity reducers. They impart excellent adhesion and flexibility retention properties to the cured coatings in which they are incorporated.

A number of methods are known for the preparation of these compounds. These methods include (a) the reaction of an hydroxyacrylate, such as 2-hydroxyethyl acrylate, and an isocyanate of the formula $R^3-N=C=O$; (b) the reaction of an hydroxyacrylate, such as 2-hydroxyethyl acrylate, with phosgene to produce a chloroformate which is subsequently reacted with ammonia to form the carbamoyloxy acrylate; (c) the reaction of an hydroxyacrylate, such as 2-hydroxyethyl acrylate, with urea; (d) the reaction of an hydroxy carbamate, such as 2-hydroxyethyl carbamate, with acryloyl chloride; and (e) the transesterification reaction between an acrylic ester and an hydroxy carbamate, such as 2-hydroxyethyl carbamate.

There are various disadvantages associated with all of the above methods of producing carbamoyloxy acrylates. For example, methods (a), (b) and (d) give high yields of the desired products, but require the use of highly toxic and/or expensive materials. Method (c) employs reaction temperatures on the order of 130° C. to achieve commercially acceptable reaction rates, but at this temperature polymerization of the acrylic moiety is difficult to prevent. We have found that method (e), using typical transesterification catalysts (e.g., tetraisopropyl titanates), sometimes produces a commercially unacceptable yield of the desired product, and these products are highly colored.

Direct esterification—reaction of acrylic or methacrylic acid with an appropriate carbamate alcohol—has generally not been employed to produce the compounds of the above formula because of the well known difficulties in esterifying higher alcohols with acrylic or methacrylic acid. The reaction conditions which tend to promote the esterification reaction also tend to promote polymerization of the acrylyl moieties. The prior art teaches preferred temperatures for esterification of "higher" alcohols (i.e., greater than 3 carbon atoms) of 95° C. and higher, such as disclosed in Canadian Pat. No. 768,651. However, the acrylate esters which are disclosed as being preparable by that process are recoverable as distillates, whereas the unsaturated carbamoyloxy carboxylates can only be conveniently recovered as residue products. This causes a problem in that the polymerization inhibitors which are effective at inhibiting polymerization of the acrylyl moiety at temperatures above 95° C. (e.g., phenothiazine, methylene blue, and hydroquinone) impart color to the product, which color is difficult or impossible to remove by means other than distillation of the product. Thus, carbamoyloxy carboxylates containing acrylyl moieties by conventional esterification processes would not be suitable for use in applications where it is desired to have a low-color product.

SUMMARY OF THE INVENTION

The present invention provides a method producing certain unsaturated carbamoyloxy carboxylates (also referred to herein as carbamoyloxy acrylates) which substantially eliminates the above disadvantages of prior art processes and allows the production of a product of low color (i.e., less than 4.0 Gardner). Additionally, this invention provides novel unsaturated carbamoyloxy carboxylates which are preparable by the process described herein.

In accordance with the process of our invention, a mono- or dihydroxyalkyl carbamate is directly esterified by reaction with acrylic or methacrylic acid at a critical temperature substantially below the preferred temperatures disclosed in the prior art for the esterification of higher alcohols. We have found that the esterification reaction can be efficiently carried out at these low temperatures in the presence of non-coloring polymerization inhibitors which are ineffective at the higher temperatures above 95° C.

Certain of the unsaturated carbamoyloxy carboxylates which can be produced by the process of this invention are of the type disclosed in U.S. Pat. No. 3,674,838, however, the process of this invention can also be used to produce compounds which are unknown in the prior art, which compounds are within the scope of this invention. More particularly, there are disclosed herein unsaturated carbamoyloxy carboxylates wherein the carbamoyl moiety is fully substituted, that is, the nitrogen heteroatom of the carbamoyl moiety has no hydrogen bonded to it. Such compounds are especially desirable in uses where it is desired that the unsaturated carbamoyloxy carboxylate contain no reactive substituents other than the acrylyl group. There are also disclosed herein novel unsaturated carbamoyloxy carboxylates which are diacrylyl functional, thus suiting them exceptionally well for use as crosslinking agents.

DETAILED DESCRIPTION OF THE INVENTION

I. THE NOVEL ESTERIFICATION PROCESS

The process of this invention for producing unsaturated carbamoyloxy carboxylates comprises esterifying an hydroxyalkyl carbamate of the formula

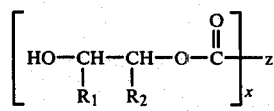

wherein x is 1 or 2 and Z is chosen from the group consisting of

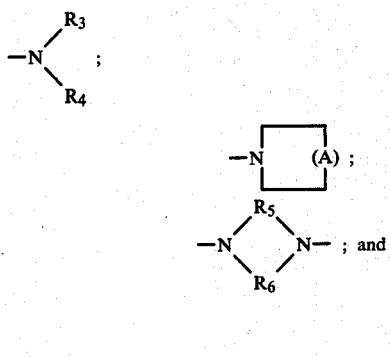

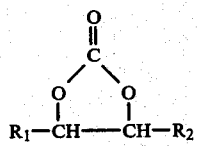

by reacting said hydroxyalkyl carbamate with acrylic or methacrylic acid at a temperature of from 40° C. to 80° C., preferably from 55° C. to 75° C. in the contact with a non-coloring lower alkoxy substituted phenolic or alkylated alkoxyphenolic polymerization inhibitor. $R_1$ and $R_2$ are each hydrogen or alkyl of 1 to 10 carbon atoms; $R_3$ is hydrogen, alkyl of up to 10 carbon atoms, or cycloalkyl of up to 10 carbon atoms; $R_4$ is alkyl of up to 10 carbon atoms, cycloalkyl of up to 10 carbon atoms, hydroxyalkyl of up to 3 carbon atoms; or aralkyl having up to 10 carbon atoms in the alkyl segment. $R_5$, $R_6$, and $R_8$ are each methylene, ethylene, or 1,2-propylene; $R_7$ and $R_9$ are each hydrogen or alkyl of up to 10 carbon atoms; and A is a divalent alkylene chair having from 2-10 carbon atoms completing a 3-6 membered ring structure.

The hydroxyalkyl carbamates described above can be conveniently produced by the reaction of a primary or secondary amine or diamine with a compound of the formula

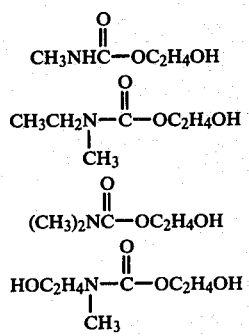

wherein $R_1$ and $R_2$ have the same meaning as above. The reaction of amines with ring compounds of this type, such as ethylene carbonate ($R_1$ and $R_2$ are both hydrogen) is known in the art (see, e.g., U.S. Pat. No. 2,441,298) and will be readily understood by the skilled worker. Illustrative of such a reaction would be the reaction of diethylamine and ethylene carbonate to produce N,N-diethyl 2-hydroxyethyl carbamate. Examples of other hydroxyalkyl carbamates useful in the process of this invention are

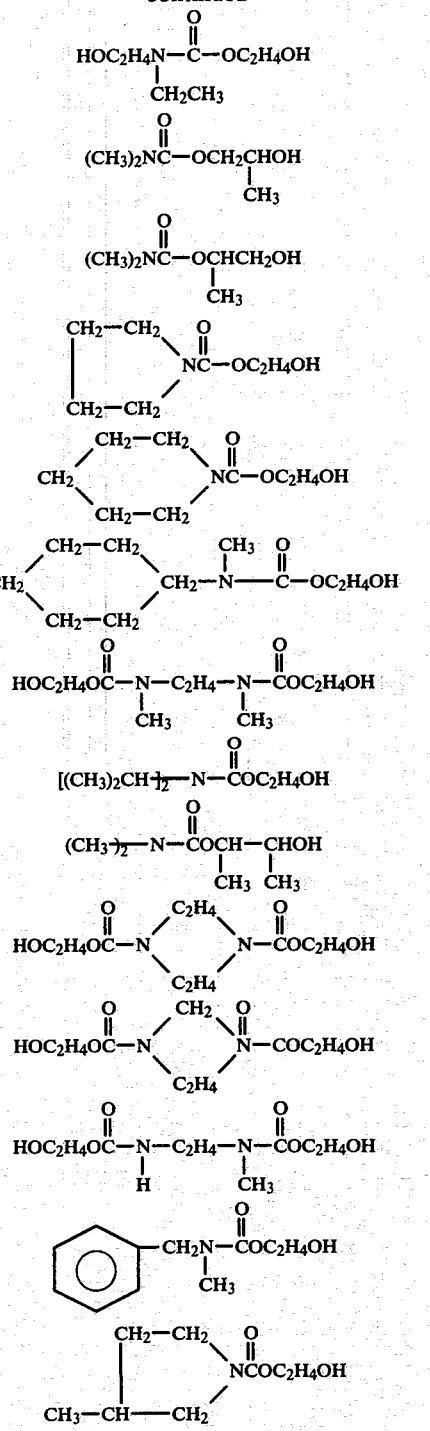

This list is meant to be illustrative only and not to exclude other compounds within the scope of the formulas above.

As previously mentioned, an essential difference between this process and prior art processes for the esterification of higher alcohols with acrylic acis is the temperature of reaction, which is from 40° C. to 80° C., and preferably from 55° C. to 75° C. in the process of our invention. The use of this relatively low reaction temperature not only allows the use of non-coloring polymerization inhibitors which would be ineffective at higher temperatures, but also reduces the possibility of degradation of the product by hydrolysis of the carbamate linkage, which occurs rapidly upon contact with water of esterification at temperatures above 90° C. in the presence of an esterification catalyst.

The acrylic or methacrylic acid and the hydroxyalkyl carbamate are reacted in a respective mole ratio of from 1:1 to about 3:1.

The polymerization is carried out with the reactants in contact with one of the acid catalysts which are known to those skilled in the art to be useful esterification catalysts. One can mention as illustrative thereof, sulfuric acid, toluenesulfonic acid, alkylsulfonic acids and hydrochloric acid. This list is not meant to exclude other suitable acid catalysts known to those skilled in the art. The skilled worker will know the concentrations at which such catalysts are effective. Typically, they are employed at concentrations from about 0.5% to 12%, based on the moles of hydroxyalkyl carbamate.

The non-coloring polymerization inhibitors employed in our process are lower alkoxy substituted phenolic or lower alkylated alkoxyphenolic inhibitors having up to 10 carbon atoms in the alkyl and alkoxy groups, which can be straight or branched chain. Those skilled in the art will recognize which polymerization inhibitors are within this definition without further description. However, one can mention as exemplary of such inhibitors the monoalkyl ethers of hydroquinone, such as monomethyl ether of hydroquinone, monoethyl ether of hydroquinone, mono-t-butyl of hydroquinone, and the like; the alkylated hydroxyanisoles, such as butylated hydroxyanisole, propylated hydroxyanisole, and the like; or mixtures of these. The preferred polymerization inhibitors are the monoalkyl ethers of hydroquinone, the most preferred being monomethyl ether of hydroquinone. The polymerization inhibitor is used at a concentration of from about 50 ppm to about 5,000 ppm, preferably from 100 ppm to 800 ppm, base on the weight of acrylic acid or methacrylic acid.

Since the efficiency of the aforementioned polymerization inhibitors is enhanced by the presence of oxygen, it is desirable to have oxygen present in the esterification reaction mixture. This can be conveniently achieved by sparging air or oxygen through the reaction mixture. Typically we sparge air through the reaction mixture at a rate of from 10 to 20 percent of the reaction mixture volume per hour.

There can be present in the esterification reaction mixture up to about 50 weight percent of a solvent which will form an azeotrope with the water of reaction, thus facilitating its separation from the carbamoyloxy acrylate. Such solvents are well known and include, for example, hexane, toluene, xylene, pentane, cyclopentane, cyclohexane, benzene or mixtures of these. In a preferred embodiment of the invention, the reaction is carried out at a temperature and pressure such that the azeotrope formed by the solvent and water of esterification is continually being vaporized and thereby removed from the reaction mixture, providing that the temperature of reaction is within the aforementioned limits of this invention. The vapor of the azeotrope can then be condensed, the water separated by any convenient means such as a Dean-Stark water separator, and the solvent recycled to the reaction mixture. By removing the water of esterification as it is formed, the possibility of hydrolysis of the carbamate linkage is further reduced.

Pressure of reaction is not critical and the reaction proceeds satisfactorily at atmospheric pressure. When one employs the above described method of azeotropically removing water of esterification during the reaction, it may be necessary to conduct the reaction at somewhat reduced pressure to vaporize the azeotrope and yet maintain the critical reaction temperature range of this process. Of course, this will depend on the particular solvent chosen and those skilled in the art will know the suitable temperatures and pressures at which the water azeotropes of various solvents can be vaporized.

The reaction is continued until substantially all of the hydroxyl groups of the hydroxyalkyl carbamate are esterified. The carbamoyloxy acrylate can be conveniently recovered by known means such as neutralization of excess acid, separation of the organic phase containing the acrylate ester, and stripping the solvent from the organic phase.

II. THE NOVEL CARBAMOYLOXY ACRYLATES

The novel carbamoyloxy acrylates of this invention have the formula $$\left[ CH_2=C(R_{10})-CO-CH(R_1)-CH(R_2)-OC(=O)- \right]_x Y$$

wherein Y is chosen from the group consisting of

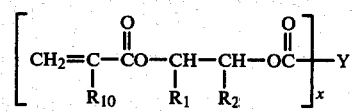

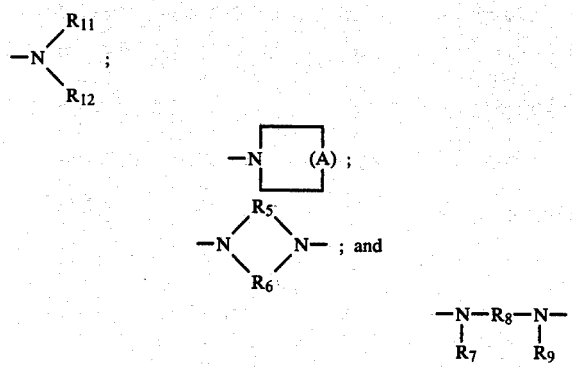

wherein x, A, $R_1$, $R_2$, $R_5$, $R_6$, $R_7$, $R_8$, and $R_9$ have the same meanings as previously described. $R_{10}$ is hydrogen or methyl; $R_{11}$ is alkyl of up to 10 carbon atoms or cycloalkyl of up to 10 carbon atoms; and $R_{12}$ is alkyl of up to 10 carbon atoms, cycloalkyl of up to 10 carbon atoms, aralkyl up to 10 carbon atoms in the alkyl segment, or

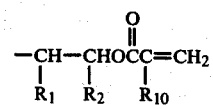

wherein $R_1$, $R_2$, and $R_{10}$ are described above.

Examples of the particular novel compounds described above are:

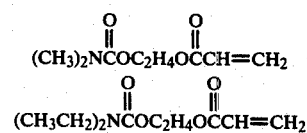

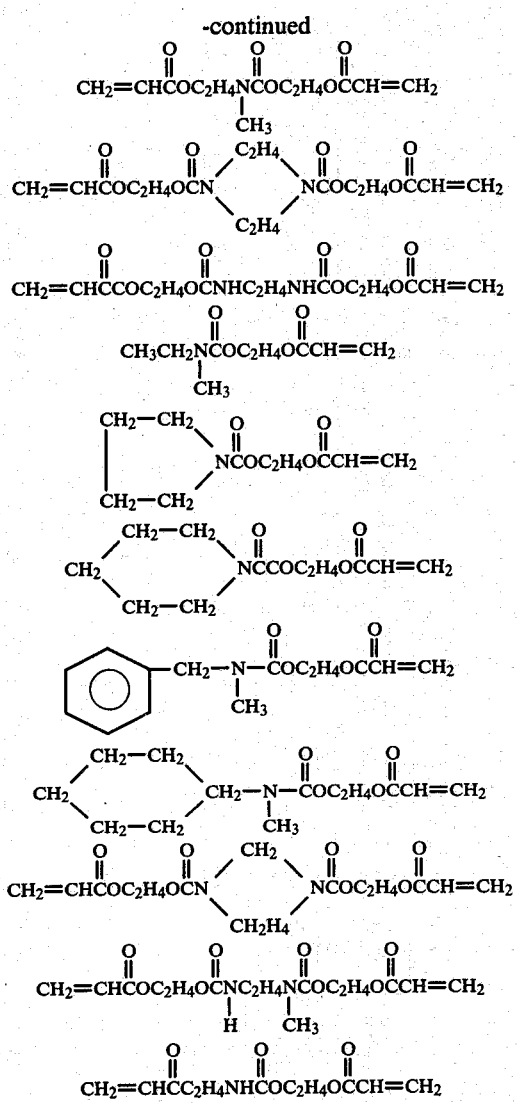

The novel carbamoyloxy acrylates can be obtained by reacting acrylic or methacrylic acid with the hydroxyalkyl carbamates described by substituting hydrogen for each acrylyl group in the above formulas describing the carbamoyloxy acrylates, in accordance with the process described herein. Compounds obtained by substituting methacrylate groups for any of the acrylyl groups in the above formulas are also exemplary of the novel compounds of this invention.

While all of the compounds of this invention can be prepared by the process described herein, it is to be understood that the scope of the novel compounds encompassed by our invention is not restricted to compounds prepared by any particular method or process.

The novel carbamoyloxy acrylates of this invention are useful in the formation of polymers, either alone or copolymerized with other ethylenically unsaturated monomers. The resultant polymers have a broad variety of uses and are especially useful in the formation of hard, mar-resistant coatings. Because of the low color obtainable in the carbamoyloxy acrylates produced by the process described herein, they are particularly useful in colorless coatings. They can be polymerized by any conventional means known for polymerizing, $\alpha,\beta$-unsaturated acid esters, including bulk, solution, suspension or emulsion methods, and they can also be polymerized by exposure to high energy radiation, such as ultraviolets, electron beam, etc.

This invention is further illustrated by the examples which follow. The examples are not intended to limit the scope of the invention in any way. Unless otherwise stated, all parts and percents are by weight. The designation MMHQ is used in lieu of the term monomethyl ether of hydroquinone.

EXAMPLE 1

To a three-neck flask fitted with a magnetic stirrer, air sparge and 5-tray Oldershaw distillation column having a Dean-Stark water separator at its overhead were charged 58.8 grams of N-methyl 2-hydroxyethyl carbamate, 40 grams of glacial acrylic acid which contained 200 ppm of MMHQ as polymerization inhibitor, an additional 200 ppm, based on the charge of acrylic acid, of MMHQ, 15.98 grams of para-toluenesulfonic acid, and 100 grams of benzene. An air sparge at the rate of 15% to 20% of the reaction mixture volume per hour was started. Pressure in the reaction vessel was reduced to about 300 mm. Hg to allow reflux of a benzene/water azeotrope. The temperature of the reactants was raised to 50° C. and maintained at that temperature throughout the reaction. After 7 hours, 4.9 grams of water of esterification had collected in the Dean-Stark water separator and gas chromatographic analysis indicated 83% of the N-methyl 2-hydroxyethyl carbamate had been esterified to form 2-(N-methyl carbamoyloxy) ethyl acrylate. The reaction mixture was cooled to room temperature, 50 ml. of saturated aqueous NaCl solution were added to reduce extraction of the desired product into the aqueous phase, and the pH was adjusted to a value of 7 by addition of 44 ml. of 20% NaOH in water solution. The residue product was isolated by separating the organic layer and stripping it of solvent at 32° C. to 50° C. under reduced pressure. The residue product weighed 57 grams and had a Gardner Color Index of 2.5.

EXAMPLE 2

Using the same apparatus as in Example 1, there were charged to the flask 119 grams of N-methyl 2-hydroxyethyl carbamate, 108 grams of glacial acrylic acid which contained 400 ppm of MMHQ as a polymerization inhibitor, 20.64 grams of para-toluenesulfonic acid and 150 grams of benzene. The temperature of the reactants was raised to 67° C. under sufficiently reduced pressure to reflux the benzene/water azeotrope which was formed. After 12 ml. of water of esterification has collected in the Dean-Stark water separator, an air sparge was started at 10% to 20% of the reaction mixture volume per hour. After about 6 hours of reaction, 14 grams of water of esterification has been collected to the Dean-Stark water separator and gas chromatographic analysis indicated that 88% of the N-methyl 2-hydroxyethyl carbamate had been esterified for form 2-(N-methyl carbamoyloxy)ethyl acrylate. The reaction mixture was cooled to room temperature and neutralized by the addition of 184 ml. of a 15% solution of NaOH in water. The residue product was isolated by separating the organic layer and stripping it of solvent at 50° C. at a reduced pressure of 4 mm. Hg. The residue product, which weighed 113.4 grams, was filtered to give 112.5 grams of a product which had a Gardner Color Index of less than 1.

EXAMPLE 3

To a three-neck flask fitted with a mechanical stirrer, an air sparge tube and a 5-tray Oldershaw distillation column having a Dean-Stark water separator at its overhead were charged 133 grams of N,N-dimethyl-2-hydroxyethyl carbamate, 20.6 grams of para-toluenesulfonic acid, 90 grams of acrylic acid which contained 400 ppm of MMHQ as a polymerization inhibitor, and 200 grams of benzene. The mixture was heated at 67° C. under sufficiently reduced presure to reflux the benzene/water azeotrope which was formed. After 6 hours of reaction, 10.3 grams of para-toluenesulfonic acid were added. After 15 hours of reaction, 14.47 grams of water of esterification had been collected in the Dean-Stark water separator. The mixture was then cooled to room temperature, 25 ml. of saturated aqueous sodium chloride solution were added, and the mixture was neutralized to pH 6.8 by addition of 97 ml. of 20% NaOH in water solution. The residue product was isolated by separating the organic layer, washing it with 25 ml. of saturated aqueous NaCl solution, stripping solvent at 30° C. to 50° C. under reduced pressure, and filtering. The filtered residue product weighed 132.4 grams. Nuclear magnetic resonance analysis indicated the predominant structure of the residue product to be

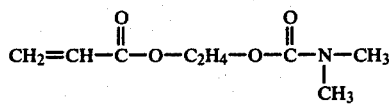

EXAMPLE 4

Using the same apparatus as in Example 3, there were charged to the flask 168 grams of N,N-diethyl-2-hydroxy ethyl carbamate, 79.2 grams of acrylic acid which contained 400 ppm of butylated hydroxyanisole as a polymerization inhibitor, 20.6 grams of para-toluenesulfonic acid, and 193 grams of hexane. The mixture was heated to 67° C. at atmospheric pressure to reflux the hexane/water azeotrope which was formed. After 9 hours of reaction, 5.2 grams of para-toluenesulfonic acid were added to the reaction mixture. After 11.5 hours, 13.2 grams of water of esterification had collected in the Dean-Stark water separator. The reaction mixture was then cooled to room temperature and 25 ml. of a saturated aqueous solution of NaCl were added. The reaction mixture was neutralized to pH 6.8 by the addition of a 20% NaOH in water solution. The organic layer was separated and the residue product was isolated by washing the organic layer with 50 ml. of saturated aqueous NaCl solution, stripping solvent under reduced presure at a peak temperature of 60° C. and filtering the remaining product. The filtered residue product weighed 160.36 grams. Nuclear magnetic resonance analysis indicated the predominant structure of the residue product to be

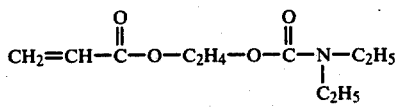

EXAMPLE 5

Using the same apparatus as in Example 3, there were charged to the flask 158.6 grams of N-2-hydroxyethyl, N-methyl 2-hydroxyethyl carbamate, 77.1 grams of acrylic acid which contained 400 ppm of MMHQ as a polymerization inhibitor, 22.1 grams of para-toluenesulfonic acid, and 250 ml. of benzene. The temperature of the reactants was raised to between 66° C. and 68° C. at sufficiently reduced pressure to reflux and the benzene/water azeotrope which was formed. After 20 hours, 26 grams of water of esterification had been collected in the Dean-Stark water separator. The reaction mixture was then cooled, 25 ml. of saturated aqueous NaCl solution were added, and the mixture was neutralized to pH 7 by the addition of a 20% NaOH in water solution. The residue product was isolated by separating the organic layer and stripping it of solvent under reduced pressure at a peak temperature of 50° C. The residue product weighed 230.9 grams. Nuclear magnetic resonance analysis indicated its structure to be

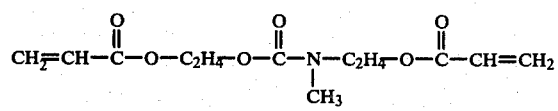

EXAMPLE 6

Using the same apparatus as in Example 3, there were charged to the flask 88 grams of ethylene carbonate and 300 ml. of benzene. The mixture in the flask was cooled to 20° C. and 30.05 grams of piperazine were added. The mixture was then heated to 55° C. over 2.5 hours and subsequently cooled to 34 ° C. over 1.75 hours. Nuclear magnetic resonance analysis of a sample of the mixture indicated the formation in the flask of

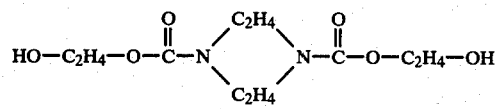

There were then added to the mixture in the flask, at a temperature of 45° C. to 50° C., 165.6 grams of acrylic acid which contained 600 ppm of MMHQ as a polymerization inhibitor, and 20.64 grams of para-toluenesulfonic acid. The temperature of the mixture was raised to 50° C. under sufficiently reduced pressure to reflux the benzene/water azeotrope which was formed. After 6 hours of reaction, 8.5 grams of water of esterification had been collected in the Dean-Stark water separator. The mixture was then stripped of solvent under reduced pressure at a peak temperature of 60° C. There were added 350 ml. of benzene and the pH was adjusted to 6.8 by the addition of 160 ml. of a 20% solution of NaOH in water. The organic layer was separated, filtered, and stripped of benzene under reduced pressure at 30° C. to 35° C. The residue product was subjected to a temperature of 50° C. at a pressure of 7 mm. Hg for 15 minutes, after which the final residue product weighed 97.5 grams. Nuclear magnetic resonance analysis indicated the predominant structure of the residue product to be

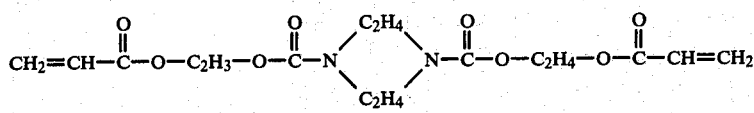

EXAMPLE 7

Using the same apparatus as in Example 3, there were charged to the flask 88 grams of ethylene carbonate, 30.05 grams of ethylene diamine, and 300 ml. of benzene at 15° C. to 20° C. The temperature rose to 30° C. and was maintained for 1.5 hours. The temperature of the mixture was then raised to 79° C. (reflux), reduced to 25° C., at which point an additional 100 ml. of benzene were added, and refluxed to 1 hour. There were then added to the mixture in the flask 93.6 grams of acrylic acid which contained 600 ppm of MMHQ as a polymerization inhibitor, and 20.6 grams of para-toluenesulfonic acid. The reaction mixture was heated to 78° C. at sufficiently reduced pressure to reflux and benzene/water azeotrope which was formed. The temperature of the mixture was reduced to 59° C. over a period of 5.5 hours, after which 16.5 grams of water of esterification had been collected in the Dean-Stark water separator. The reaction mixture was cooled to room temperature, 25 ml. of a saturated aqueous NaCl solution were added to the mixture, and the mixture was neutralized to pH 6.8 by the addition of 122 ml. of a 20% solution of NaOH in water. The organic layer was separated and 69.1 grams of a solid material which melted at 50° C. was removed from the organic layer. An additional 13.9 grams of solid material were isolated by stripping solvent from the organic layer under reduced pressure at 32° C. to 35° C. Nuclear magnetic resonance analysis of both solid fractions isolated from the organic layer indicated the predominant structure to be

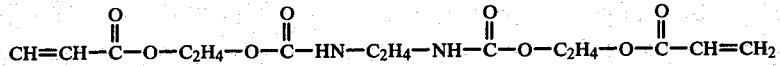

What is claimed is:

1. A carbamoyloxy acrylate compound of the formula

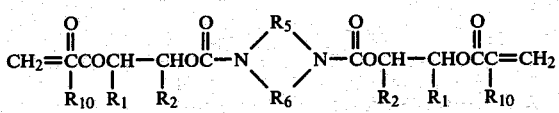

wherein $R_1$ and $R_2$ are each hydrogen or alkyl of up to 10 carbon atoms; $R_5$ and $R_6$ are each methylene, ethylene, or 1,2-propylene; and $R_{10}$ is hydrogen or methyl.

2. The compound of the formula

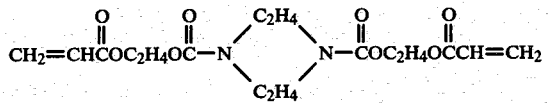

* * * * *

UNITED STATES PATENT AND TRADEMARK OFFICE
CERTIFICATE OF CORRECTION

PATENT NO. : 4,167,635
DATED : September 11, 1979
INVENTOR(S) : Frank G. Cowherd, III; Louis F. Theiling, Jr.

It is certified that error appears in the above-identified patent and that said Letters Patent are hereby corrected as shown below:

Column 4, the eleventh formula from the top should read:

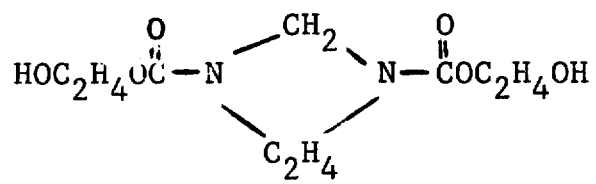

Column 7, the ninth formula from the top should read:

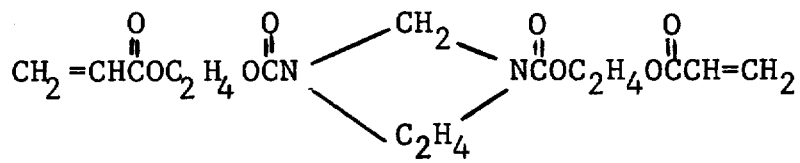

UNITED STATES PATENT AND TRADEMARK OFFICE
CERTIFICATE OF CORRECTION

PATENT NO. : 4,167,635
DATED : September 11, 1979
INVENTOR(S) : Frank G. Cowherd, III; Louis F. Theiling, Jr.

It is certified that error appears in the above-identified patent and that said Letters Patent are hereby corrected as shown below:

Column 11, the formula in Example 6 should read:

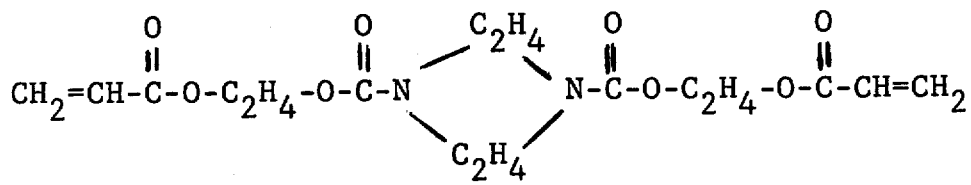

Column 12, the formula in Example 7 should read:

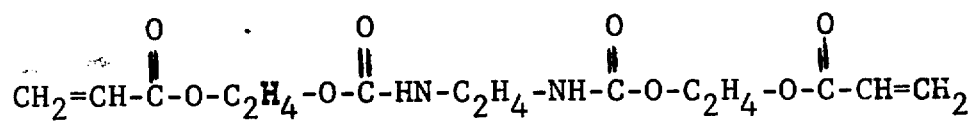

Claim 1, the formula should read:

UNITED STATES PATENT AND TRADEMARK OFFICE
CERTIFICATE OF CORRECTION

PATENT NO. : 4,167,635
DATED : September 11, 1979
INVENTOR(S) : Frank G. Cowherd, III; Louis F. Theiling, Jr.

Page 3 of 3

It is certified that error appears in the above-identified patent and that said Letters Patent are hereby corrected as shown below:

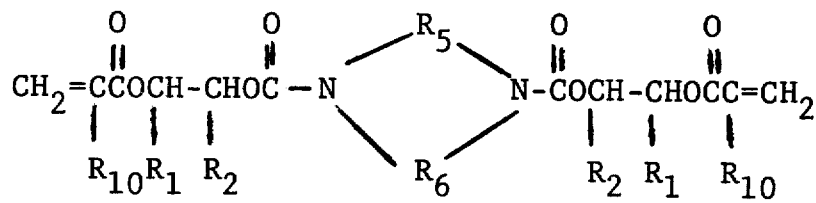

Signed and Sealed this

Eighth Day of January 1980

[SEAL]

Attest:

SIDNEY A. DIAMOND

*Attesting Officer*   *Commissioner of Patents and Trademarks*